(12) United States Patent
Valenti

(10) Patent No.: US 8,945,077 B2
(45) Date of Patent: Feb. 3, 2015

(54) FEMALE URINATION DEVICE WITH A RETRACTABLE TIP

(71) Applicant: Vema LLC, Brooklyn, NY (US)

(72) Inventor: Vincent Valenti, Brooklyn, NY (US)

(73) Assignee: Vema LLC, Brooklyn, NY (US)

( * ) Notice: Subject to any disclaimer, the term of this patent is extended or adjusted under 35 U.S.C. 154(b) by 0 days.

(21) Appl. No.: 13/889,739

(22) Filed: May 8, 2013

(65) Prior Publication Data

US 2013/0239311 A1 Sep. 19, 2013

Related U.S. Application Data

(63) Continuation-in-part of application No. 13/229,578, filed on Sep. 9, 2011, now abandoned.

(51) Int. Cl.
*A61F 5/44* (2006.01)
*A61F 5/455* (2006.01)
*A61F 5/37* (2006.01)

(52) U.S. Cl.
CPC ............ *A61F 5/4556* (2013.01); *A61F 5/3746* (2013.01)
USPC ............ 604/347; 604/317; 604/327; 604/346

(58) Field of Classification Search
None
See application file for complete search history.

(56) References Cited

U.S. PATENT DOCUMENTS

| 2,278,486 | A |   | 3/1959 | Bartlett et al. |
| 4,453,938 | A |   | 6/1984 | Brendling |
| 4,681,573 | A | * | 7/1987 | McGovern et al. ............ 604/329 |
| 5,243,712 | A | * | 9/1993 | Cross .............................. 4/144.2 |
| 5,408,703 | A |   | 4/1995 | Cicio |
| 5,966,748 | A |   | 10/1999 | Young et al. |
| 6,202,225 | B1 | * | 3/2001 | Beck et al. ....................... 4/144.2 |
| 6,375,643 | B1 | * | 4/2002 | Moorhead et al. ............. 604/322 |
| 6,493,884 | B1 | * | 12/2002 | Muller et al. .................... 4/144.2 |
| 6,719,741 | B2 |   | 4/2004 | Ching |
| D495,798 | S | * | 9/2004 | Gugliotta ..................... D24/122 |
| D527,101 | S |   | 8/2006 | Fernandez |
| 7,131,149 | B2 |   | 11/2006 | Langford |
| 7,325,256 | B1 | * | 2/2008 | Pecinka, Sr. .................... 4/144.1 |
| 2007/0185466 | A1 | * | 8/2007 | Co ................................. 604/349 |
| 2007/0191795 | A1 |   | 8/2007 | Di Croce |

* cited by examiner

*Primary Examiner* — Tan-Uyen (Jackie) T Ho
*Assistant Examiner* — Eric Bryant
(74) *Attorney, Agent, or Firm* — Im IP Law PLLC; C. Andrew Im

(57) ABSTRACT

The female urination device assists a female in urinating from a standing position and directs the urine a suitable distance from the female. The device comprises a first end having a first opening for discharging urine and a second end having a second opening for receiving the urine. The second opening is larger than the first opening. The device further comprises a retractable tip to extend the length of the device.

10 Claims, 5 Drawing Sheets

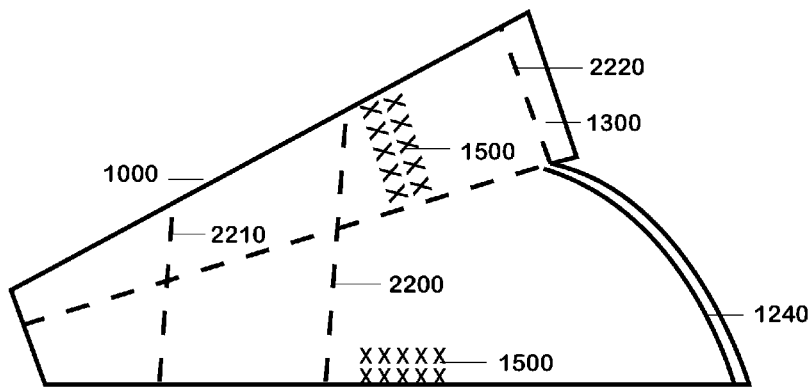
FIG. 4A
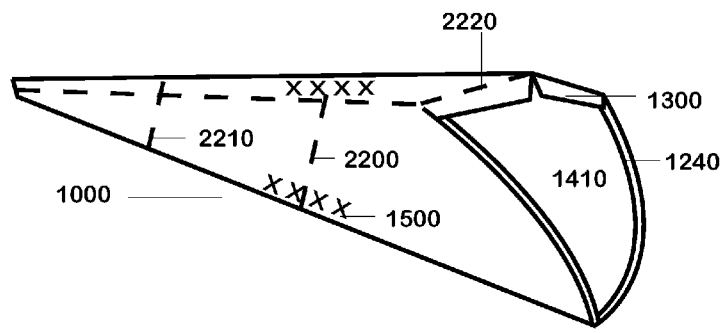
FIG. 4B
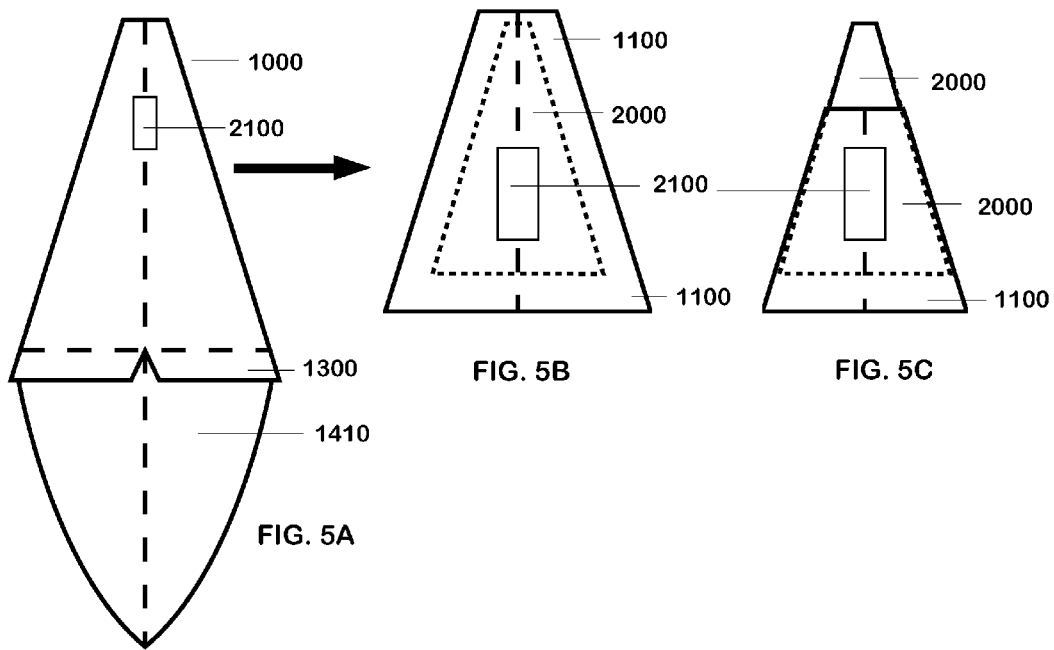
FIG. 5A
FIG. 5B
FIG. 5C

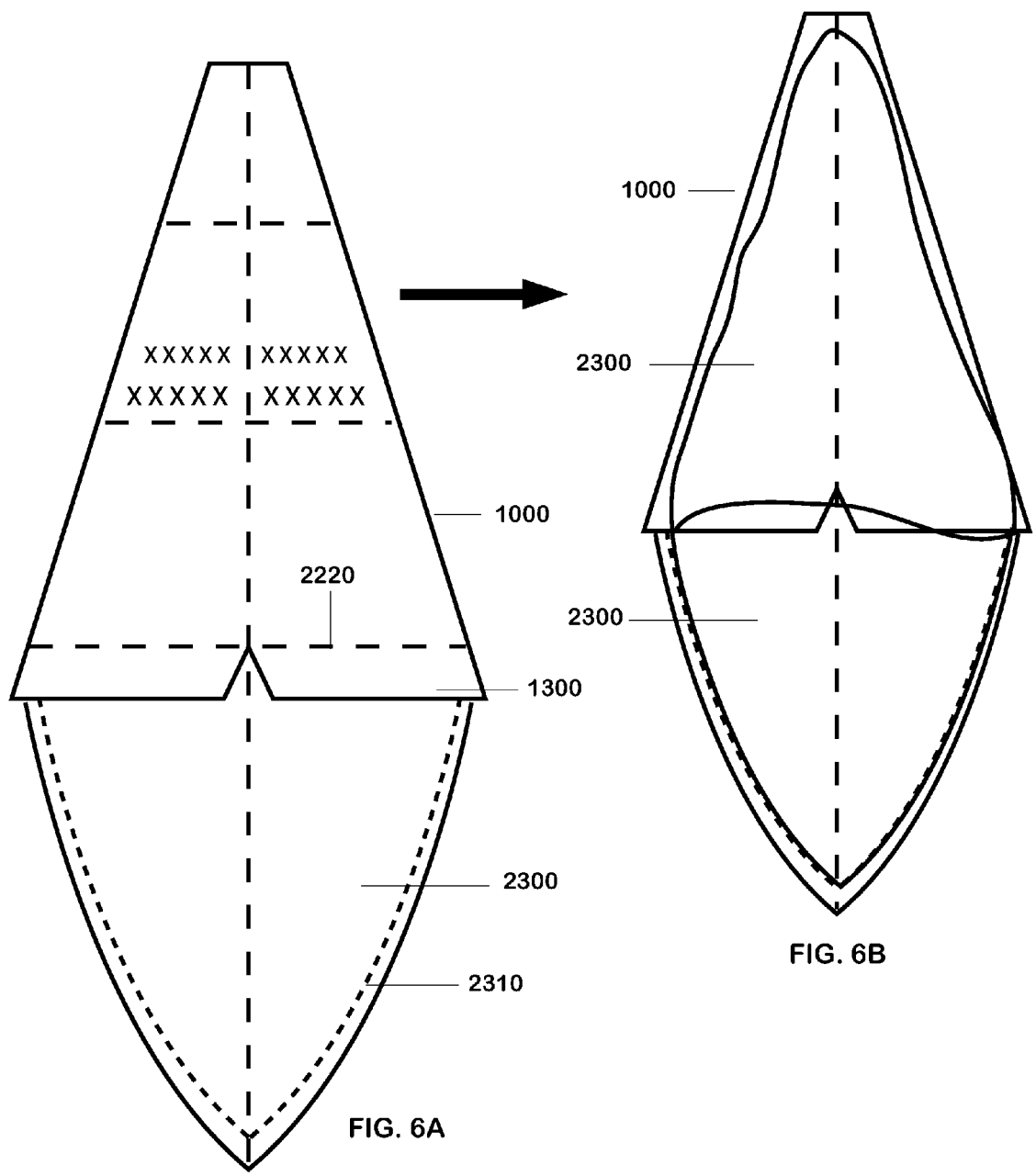

FEMALE URINATION DEVICE WITH A RETRACTABLE TIP

RELATED APPLICATION

The present application is a continuation-in-part application of U.S. application Ser. No. 13/229,578 filed Sep. 9, 2011, which is incorporated herein by reference in its entirety.

TECHNICAL FIELD

The claimed invention relates to female urination device, and more particularly, to female urination devices which allow a female to urinate from a standing position.

BACKGROUND OF THE INVENTION

Public restrooms for women are very often unclean and unsanitary. The toilet seats in public restrooms are often dirty or otherwise in an unsanitary condition. Because of this, women often squat above the toilet seat when using the public restroom to avoid touching the toilet seat. This can be difficult and unpleasant way for a woman to urinate, especially for a young girl. Similarly, women may have no choice but to squat while holding her clothing out of the way in order to urinate when no restroom is available while traveling, hiking or camping.

In prior art, various types of female urination devices have been proposed. However, many of these devices are complicated and cumbersome to use. Also, none of these devices provide a retractable tip to lengthen the device or an aperture controller to adjust the size of the opening to accommodate users' different body sizes. Further, none of these devices provide an inner lining to facilitate urine collection, e.g., to provide urine sample in a doctor's office. This is a particular problem because many of these devices are constructed biodegradable paper that can be flushed in a toilet, see, e.g., U.S. Pat. No. 5,480,703.

Additionally U.S. Pat. No. 5,966,748 requires the user to wrap a flat sheet of material to form a funnel shaped device and the sanitary pad is susceptible to contamination during use because of its proximity to the anal area.

Further U.S. Pat. No. 4,681,573 requires two hands to prepare the collapsible device for use. One hand to hold the device while using the other hand to push the top portion of the device upward and the bottom portion of the device downward, or alternatively, one hand to push the top portion of the device upward and the other hand to push the bottom portion of the device downward. Also, U.S. Pat. No. 2,878,486 requires two hands to open the device for use from its unfolded position. The device is held in an opened hand with thumb and fingers and the handle portions are pulled in an upward direction with the fingers of the other hand until opened. It is preferable that only one hand is required to use and operate device.

OBJECT AND SUMMARY OF THE INVENTION

Therefore, it is an object of the claimed invention to solve the aforementioned problems with the conventional female urination device.

Another object of the claimed invention is to provide a female urination device which is simple, easy to use and convenient to carry.

In accordance with an exemplary embodiment of the claimed invention, the female urination device assist a female in urinating from a standing position and for directing the urine a suitable distance from the female. The first end of the device has a first opening for discharging urine, and the second end has a second opening for receiving the urine and is larger than the first opening. The device comprises a retractable tip for extending the first end to lengthen the device and a retraction tab for sliding the retractable tip in and out of the first end. The retraction tab is slidable towards the first end to slide the retractable tip out of the first end to increase a length of the device and slidable away from the first end to retract the retractable tip into the first end.

In accordance with an exemplary embodiment of the claimed invention, the aforesaid device further comprises an aperture controller to adjust the size of the second opening, and preferably, a tear line to tear or remove the aperture controller from the device.

In accordance with an exemplary embodiment of the claimed invention, the aforesaid device further comprises a lining or bag inside the device to collect urine. Preferably, the lining or bag is attached to the device with a tear line to facilitate removable of the lining or bag from the device.

In accordance with an exemplary embodiment of the claimed invention, the second end of the aforesaid device is coated with non-abrasive wax or paper; and wherein the lower portion of the second end is concave in shape to provide a tight contoured fit.

In accordance with an exemplary embodiment of the claimed invention, the second end of the aforesaid device comprises a rolling part to provide a smooth second end to eliminate sharp edges and to provide a sealed perimeter at the second end to contain the urine within the device In accordance with an exemplary embodiment of the claimed invention, the aforesaid device further comprises a gripping portion on the exterior surface of the device. The gripping portion comprises a rough surface or rubberized coating providing friction to prevent slippage and to operate the device with a user's one hand.

In accordance with an exemplary embodiment of the claimed invention, the aforesaid device further comprises a score line between the first and second end to fold the device in half for a compact fit.

In accordance with an exemplary embodiment of the claimed invention, the aforesaid device further comprises a score line towards the first end to fold the first end after use to prevent any leakage from spilling out.

In accordance with an exemplary embodiment of the claimed invention, the female urination device assist a female in urinating from a standing position and for directing the urine a suitable distance from the female. The first end of the device has a first opening for discharging urine, and the second end has a second opening for receiving the urine and is larger than the first opening. The device further comprises a lining or bag inside the device to collect the urine, such as urine sample for use in the doctor's office. The lining or bag is attached to the device with a tear line to facilitate removable of the lining or bag from the device.

In accordance with an exemplary embodiment of the claimed invention, the aforesaid device further a retractable tip for extending the first end to lengthen the device, and preferably, a retraction tab for sliding the retractable tip in and out of the first end. The retraction tab is slidable towards the first end to slide the retractable tip out of the first end to increase a length of the device and slidable away from the first end to retract the retractable tip into the first end.

In accordance with an exemplary embodiment of the claimed invention, the aforesaid device further comprises a sanitary wipe removably attached to an exterior surface of the device.

In accordance with an exemplary embodiment of the claimed invention, the aforesaid device is made from a biodegradable and water-resistant material.

In accordance with an exemplary embodiment of the claimed invention, the interior surfaces of the aforesaid device are coated with water-resistant coating, epoxy or synthetic resin.

In accordance with an exemplary embodiment of the claimed invention, the aforesaid device is funnel shaped in an open useable configuration.

Various other objects, advantages and features of the claimed invention will become readily apparent from the ensuing detailed description. Novel features will be emphatically pointed out in the appended claims.

BRIEF DESCRIPTION OF THE DRAWINGS

The claimed invention is further explained in the description which follows with reference to the drawings, illustrations illustrating, by way of non-limiting examples, various embodiments of the invention, with like reference numerals representing similar parts throughout the several views, and wherein:

FIG. 4A-4B show side and perspective views of the device with score lines to fold the device for storage and/or the tip to prevent leakage after use in accordance with an exemplary embodiment of the claimed invention;

FIG. 5A-C show top and exploded views of the device with retractable tip in accordance with an exemplary embodiment of the claimed invention;

FIG. 6A-B show top and exploded views of the device with a disposable bag inside the device to collect urine in accordance with an exemplary embodiment of the claimed invention.

DETAILED DESCRIPTION OF THE EMBODIMENTS

As illustrated in FIGS. 1-6, the female urination device 1000 is designed to assist a female to urinate in a standing position, thereby enabling the female to comfortably and safely urinate while minimizing hygiene risks under any conditions, such as unsanitary restrooms and no available public facilities.

In accordance with an exemplary embodiment of the claimed invention, the device 1000 comprises two opposing upper panels 1100 and two opposing lower panels 1200. The upper panel 1100 is defined by an upper longitudinal crease 1110 and a side longitudinal crease 1120. The lower panel 1200 is defined by a lower longitudinal crease 1210 and a side longitudinal crease 1120. These panels 1100, 1200 can be made of any suitable, water-resistant, pliable material, such as paper, cardboard, plastic and the like. Alternatively, the interior surfaces or both interior and exterior surfaces of the panels 1100, 1200 can be coated with a thin, water-resistant coating, epoxy or synthetic resin to prevent the urine passing through the device 1000 from leaking through the panels 1100, 1200.

Although many of the prior urination device is made from a biodegradable material that can be flushed downed the toilet after use, such devices are too flimsy and not sturdy enough to provide adequate protection during use. Accordingly, the claimed device 1000 is preferably made of sturdy biodegradable material that can be disposed of in any conventional manner, e.g., a waste receptacle, without any adverse environmental effect.

Figure 1:
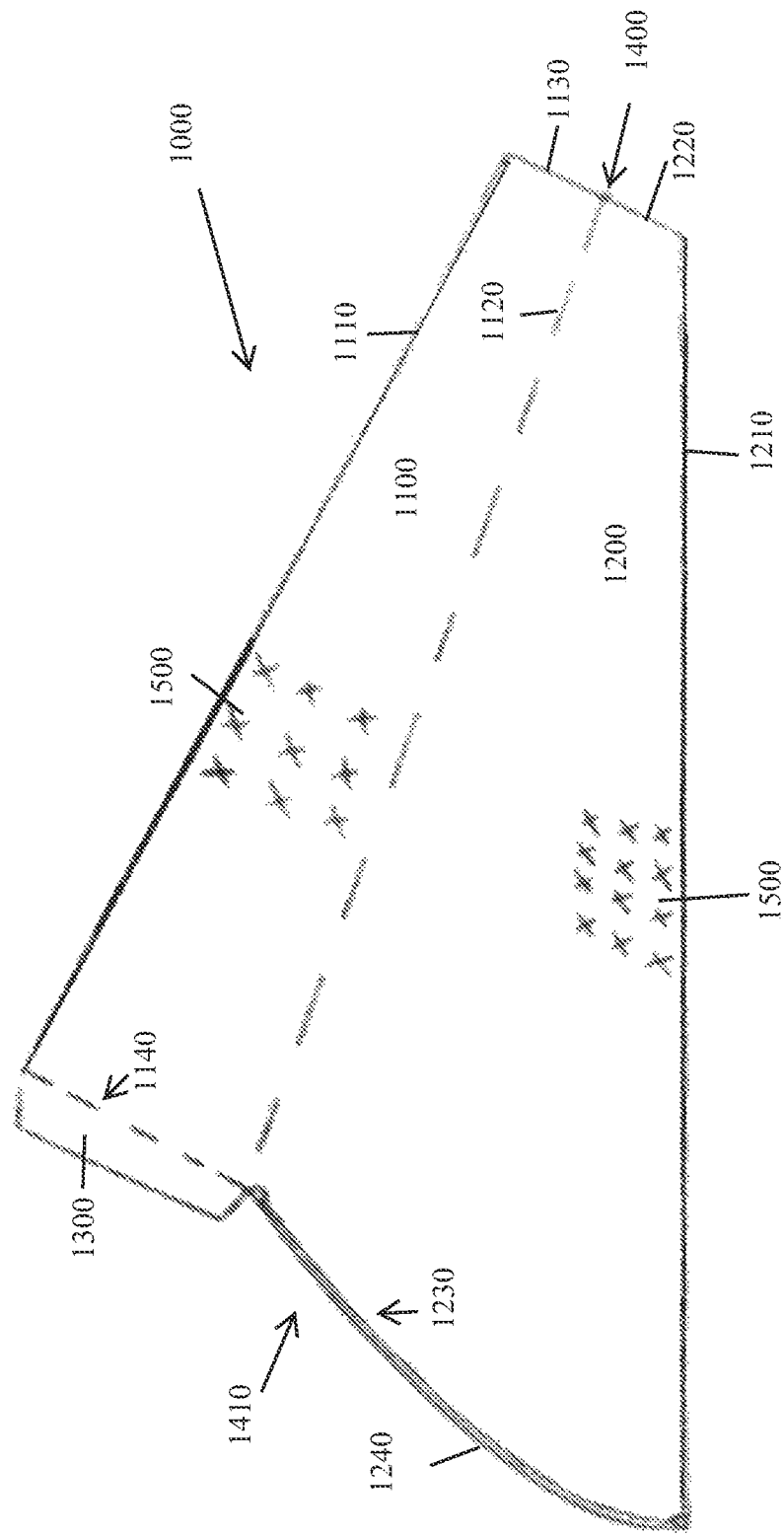
FIG. 1 shows a side view of the device with an aperture controller and a smooth second end in a closed or flat configuration in accordance exemplary embodiment of the claimed invention.

The device 1000 is preferably constructed from a blank, not shown, wherein longitudinal creases 1110, 1120, 1210 are scored on the blank. The device 1000 is preferably packaged in a closed or a flat configuration as shown in FIG. 1. The flat or closed configuration of the device 1000 enables it to be conveniently carried in a purse or pocketbook, and, therefore, readily available at all times. Preferably, one of the upper panels 1100 comprises a strip (not shown) for attaching the strip to the opposing upper panel 1100 by glue or other comparable means.

Each of the two opposing lower panels 1200 has a first end 1220 and a second end 1230. Preferably, the second end 1230 is concave and covered with non-abrasive paper or wax to provide a comfortable and tight contoured fit around the woman's vulva when the device is held in place during use. In accordance with an exemplary embodiment of the claimed invention, the second end 1230 comprises a rolling part 1240 to provide a non-abrasive, smooth curved second end 1230, thereby eliminating any sharp edges touching the user and alleviating any potential discomfort or irritation to the user's body during use.

Figure 2:
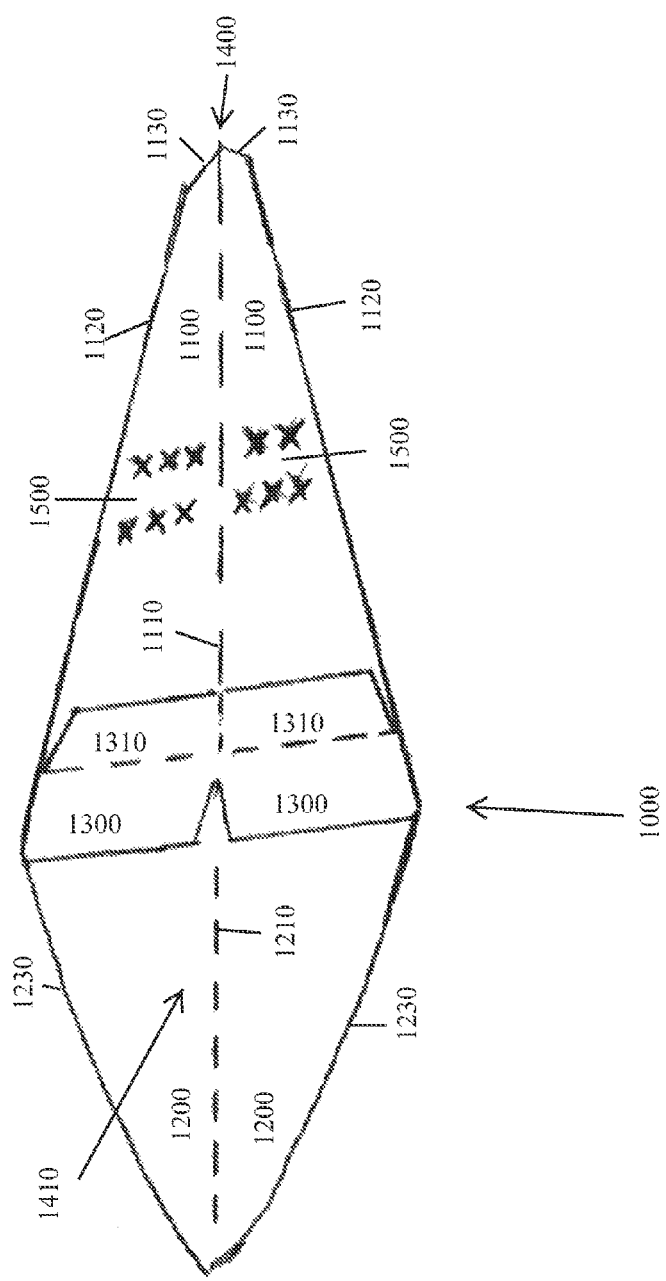
FIG. 2 shows a perspective view of the device with a dual aperture controller in an open or useable configuration with in accordance with an exemplary embodiment of the claimed invention.

Each of the two opposing upper panels 1100 has a first end 1130 and a second end 1140. In accordance with an exemplary embodiment of the claimed invention, the second end 1140 of the upper panels 1100 comprises an aperture controller 1300 to protect adjust the size of the second opening 1410. The rolling part 1240 of the second end 1230 provide a comfortable, sealed perimeter around the vulva to protect the user from accidental leakage or spillage during use. Also, the aperture controller 1300 can be torn or removed along the tear line 2220 if not needed or desired by the user. Preferably, the upper panels 1100 can additionally comprise a second aperture controller 1310 (as shown in FIG. 2) which works with the aperture controller 1310 to further enlarge the second opening 1410. Furthermore, the rolling part 1240 and the aperture controller 1300 eliminate any sharp edges touching the user, thereby minimizing any potential discomfort or irritation to the user's body during use.

The user applies pressure to both the lower longitudinal crease 1210 and the upper longitudinal crease 1100 of the device 1000 in a closed configuration (see, e.g., FIG. 1) using one hand to open the device 1000 to a useable configuration and utilizing the aperture controller guard 1300 (see, e.g., FIGS. 2 and 3) to adjust the second opening 1410. The pressure applied by the fingers of the user's hand pushes the upper longitudinal crease 1100 and the lower longitudinal crease 1210 towards each other to deploy the female urination device 1000. That is, the female urination device 1000 moves from the closed/flat configuration to the opened/useable configuration. It is appreciated that only one hand is needed to open the device 1000, thereby leaving the other hand free. When the device 1000 is opened, the aperture controller 1300 can be deployed to adjust the size of the second opening 1410 to accommodate different body dimensions of the users, thereby providing an one-sized device 1000 to fit a multitude of users having varying bodily dimensions. In accordance with an exemplary embodiment of the claimed invention, the aperture controller 1300 can be deployed downward or towards to decrease the size of the second opening 1410, as exemplary shown in FIG. 4B, to decrease the size of the second opening 1410 or can be deployed upwards to increase the size of the second opening 1410. That is, the aperture controller 1300 provides a custom fit by enabling the user to control the size of the second opening 1410, thereby preventing or minimizing accidental leaking or spillage during use.

In the opened/useable configuration, the second ends 1140 of the opposing upper panels 1100 and the second ends 1230 of the opposing lower panels 1200 form a second opening 1410. The second opening 1410 of the device 1000 is placed around the woman's vulva to permit the woman to urinate from a standing position. Preferably, the size of the second opening 1410 is adjusted using the aperture controller 1300 before the device is placed around the user's vulva. In accordance with an exemplary embodiment of the claimed invention, the device 1000 is used such that the aperture controller 1300 is at the top of the device 1000 and the opposing lower panels 1200 is at the bottom of the device 1000 to direct the urine to the first opening 1400 and to provide a comfortable, tight contoured fit around the vulva by the rolling part 1240 of the concave second end 1230.

In the opened/useable configuration, the device 1000 resembles a funnel with the first ends 1130 of the opposing upper panels 1100 and the first ends 1220 of the opposing lower panels 1200 forming a first opening 1400. The urine travels down the interior channel 1420 of the device 1000 and exits the device 1000 away from the user through the first opening 1400. Preferably, the first opening is angled such that the opposing upper panels 1100 extends beyond the lower panels 1200 to prevent the exiting urine from splashing upward.

Figure 3:
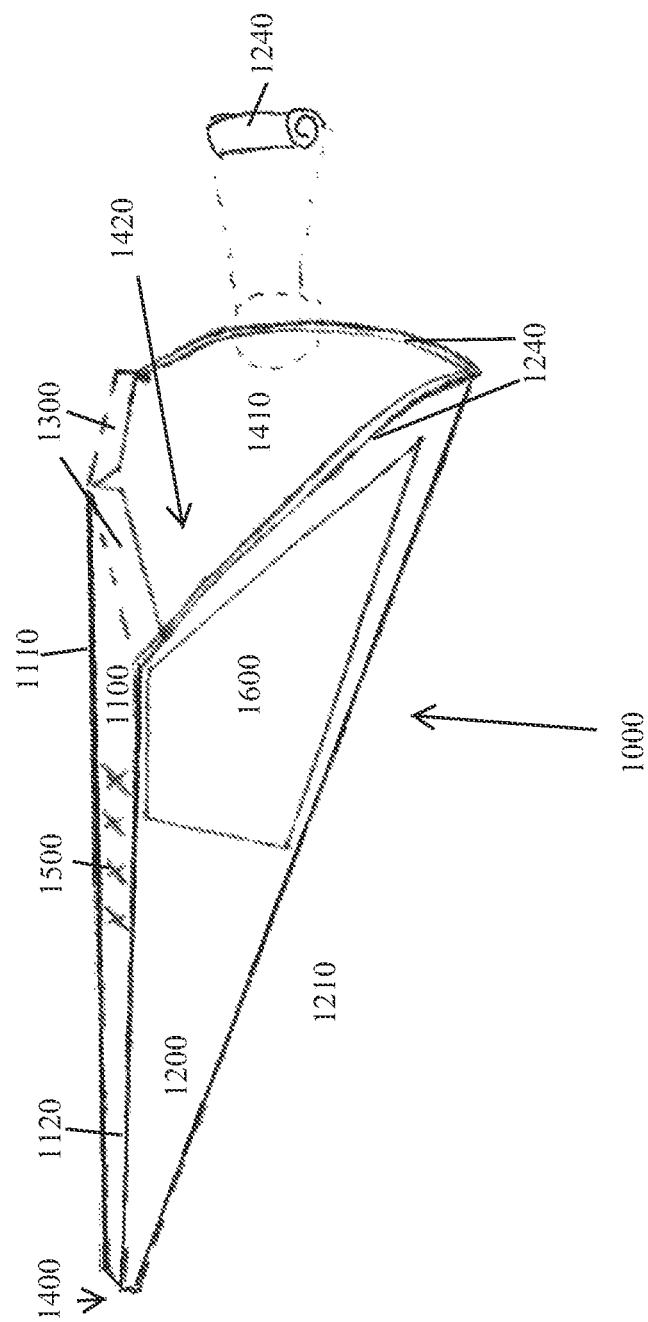
FIG. 3 shows a perspective view of the device with an aperture controller deployed to reduce the size of the opening and a smooth second end in an open or useable configuration in accordance with an exemplary embodiment of the claimed invention.

In accordance with an exemplary embodiment of the claimed invention, as shown in FIGS. 1-3, the exterior surfaces of the opposing upper panels 1100 and/or opposing low panels 1200 comprises a gripping portion 1500 to prevent the device 1000 slipping from the user's hand during use. The gripping portion 1500 can comprise a rough surface, a rubberized coating and the like to provide sufficient friction to prevent slippage during use.

In accordance embodiment of the claimed invention, as shown in FIG. 3, the device 100 comprises a sanitary wipe 1600 which is removably attached to the exterior surface of the device 1000, e.g., to the exterior surface of one of the opposing lower panels 1200 or one of the opposing upper panels 1100. The sanitary wipe 1600 is preferably made of biodegradable material. The sanitary wipe 1600 can be peeled off from the device 1000 to dry the area after the user has finished urinating. This provides the user with the additional convenience of carrying an uncontaminated wipe to dry herself with after using the device 1000, particularly in a remote area where no public facilities are available.

In accordance with an exemplary embodiment of the claimed invention, as exemplary shown in FIGS. 4A-4B, the female urination device 1000 comprises a score line or crease 2200 across the middle of the upper and lower panels 1100, 1200 (i.e., between the first end 1400 and the second end 1410) to fold the device 1000 in half. This advantageously enables the user to fold the device 100 for a more compact fit in their purse. Alternatively, the manufacturer or supplier of the claimed device 1000 can package the device in a smaller package by folding the device by the score line 2200 and the user can unfold the device 1000 for use.

In accordance with an exemplary embodiment of the claimed invention, as exemplary shown in FIGS. 4A-4B, the female urination device 1000 comprises a score line or crease 2210 towards the tip or the first opening 1400, preferably between the first opening 1400 and the score line 2200. After the device 100 is used, the user can fold the device 1000 by the score line 2210 to prevent any leakage from spilling out while disposing of the device 1000.

In accordance with an exemplary embodiment of the claimed invention, as exemplary shown in FIGS. 5A-C, the female urination device 1000 comprises a retractable tip 2000 to adjust the length of the device 1000 and a tab 2100 connected to the retractable tip 2000. The user can slide the retraction tab 2100 towards the first opening 1400 to extend the retractable tip 2000 out through the first opening 1400 or slide the tab 2100 away from the first opening 1400 to retract the retractable tip 2000 back inside the device 1000 through the first opening 1400. For example, the retractable tip 2000 can be used by the user to shorten the distance from the device 1000 to the urinal or toilet, such as to accommodate a taller user.

In accordance with an exemplary embodiment of the claimed invention, as exemplary shown in FIGS. 6A-B, the female urination device 100 comprises a lining or bag 2300 inside the device 1000. The bag 2300, such as a plastic bag, can be used for urine collection, e.g., collecting urine samples in a doctor's office. After use, the lining or bag can be torn or removed along the tear line 2310 by the user.

Although the claimed invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the claimed invention described in the specification.

What is claimed:

1. A disposable device for assisting a female in urinating from a standing position and for directing urine a distance from the female, comprising:
    two collapsible opposing upper panels forming an upper longitudinal crease and two collapsible opposing lower panels forming a lower longitudinal crease, the upper longitudinal crease and the lower longitudinal crease move towards each other in response to a pressure applied thereto to deploy the disposal device by forming an elongated shaped funnel;
    a first end of the elongated shaped funnel having a first opening for discharging urine;
    a second end of the elongated shaped funnel having a second opening for receiving the urine and being larger than the first opening;
    a retractable tip for extending the first end of the elongated shaped funnel to lengthen the disposable device; and
    a retraction tab for sliding the retractable tip in and out of the first opening of the elongated shaped funnel, the retraction tab is slidable towards the first opening to slide the retractable tip out of the first opening to increase a length of the first end of the disposable device and slidable away from the first opening to retract the retractable tip into the first opening.

2. The disposable device of claim 1, further comprising an aperture controller for adjusting a size of the second opening.

3. The disposable device of claim 2, further comprising a tear line to tear or remove the aperture controller from the disposable device.

4. The disposable device of claim 1, further comprising a lining or bag inside the disposable device to collect the urine.

5. The disposable device of claim 4, wherein the lining or bag is attached to the disposable device with a tear line to facilitate removable of the lining or bag from the disposable device.

6. The disposable device of claim 1, wherein the second end is coated with non-abrasive wax or paper; and wherein a lower portion of the second end is concave in shape to provide a tight contoured fit.

7. The disposable device of claim 1, wherein the second end further comprises a rolling part to provide a smooth second end to eliminate sharp edges and to provide a sealed perimeter at the second end to contain the urine within the disposable device.

8. The disposable device of claim 1, further comprising a gripping portion on an exterior surface of the disposable device comprising a rough surface or rubberized coating providing friction to prevent slippage and configured to operate the disposable device with a user's one hand.

9. The disposable device of claim 1, further comprises a score line between the first and second end to fold the disposable device in half for a compact fit.

10. The disposable device of claim 1, further comprises a score line towards the first end to fold the first end after use to prevent any leakage from spilling out.

* * * * *